US010365279B2

(12) United States Patent
Narain et al.

(10) Patent No.: US 10,365,279 B2
(45) Date of Patent: Jul. 30, 2019

(54) ASSAY SYSTEM FOR THE ASSESSMENT OF ONCOGENICITY, TUMOR PROGRESSION, AND TREATMENT EFFICACY (75) Inventors: Niven Rajin Narain, Cambridge, MA (US); Indushekhar Persaud, Homestead, FL (US)

(73) Assignee: Berg LLC, Framingham, MA (US)

( * ) Notice: Subject to any disclaimer, the term of this patent is extended or adjusted under 35 U.S.C. 154(b) by 0 days.

(21) Appl. No.: 12/864,185

(22) PCT Filed: Jan. 26, 2009

(86) PCT No.: PCT/US2009/031957
§ 371 (c)(1),
(2), (4) Date: Oct. 18, 2010

(87) PCT Pub. No.: WO2009/094619
PCT Pub. Date: Jul. 30, 2009

(65) Prior Publication Data
US 2011/0027811 A1    Feb. 3, 2011

Related U.S. Application Data (60) Provisional application No. 61/023,570, filed on Jan. 25, 2008.

(51) Int. Cl.
G01N 33/573    (2006.01)
A61K 39/00    (2006.01)
G01N 33/574    (2006.01)

(52) U.S. Cl.
CPC .................................. G01N 33/574 (2013.01)

(58) Field of Classification Search
None
See application file for complete search history.

(56) References Cited

U.S. PATENT DOCUMENTS

| | | | |
|---|---|---|---|
| 7,056,660 | B1 | 6/2006 | Giesing et al. |
| 2003/0138792 | A1 | 7/2003 | Schlegel et al. |
| 2003/0235816 | A1 | 12/2003 | Slawin et al. |
| 2004/0133352 | A1 | 7/2004 | Bevilacqua et al. |
| 2006/0093575 | A1 | 5/2006 | Pau et al. |
| 2007/0190529 | A1 | 8/2007 | Ridder et al. |

FOREIGN PATENT DOCUMENTS

| | | |
|---|---|---|
| WO | WO-1999010528 A1 | 3/1999 |
| WO | WO-2002037113 A2 | 5/2002 |
| WO | WO 2003/040404 | 5/2003 |
| WO | 03106974 A2 | 12/2003 |
| WO | 2005094322 A2 | 10/2005 |
| WO | 2006/022895 A2 | 3/2006 |
| WO | 2005103281 A3 | 4/2006 |
| WO | 2006043938 A1 | 4/2006 |
| WO | 2007137187 A2 | 11/2007 |

OTHER PUBLICATIONS

Eissa et al Clinical Chemistry 44: 7, p. 1423-1429 1998.*
Zhou et al, Cancer Letter 237:10-21, 2006.*
Shinhal et al, Clin Can Res 11: 3974-3986, 2005.*
Martin et al, Cytokine 11:80-82, 1999 (only p. 80-82).*
Prokop et al, Leukemia 14:1606-13, 2000, abstract.*
Wu et al, Anticancer Res 16:2233-9, 1996, abstract.*
Huang et al, Would J of Gastroenterology, 10:43-470, 2004.*
Yang et al, Science, 275: 1129-1132, 1997.*
Ahmed, "Molecular markers that predict response to colon cancer therapy," *Exp. Rev. Mol. Diag.*, Future Drugs, London, GB, 5(3):353-375 (2005).
Garcea et al., "Molecular prognostic markers in pancreatic cancer: A systematic review," *Euro. J. Cancer*, 41:2213-2236 (2005).
Zisman et al.,"LABAZ1: A metastatic tumor model for renal cell carcinoma expressing the carbonic anhydrase type 9 tumor antigen," *Cancer Res.*, 63(16):4952-4959 (2003).
International Search Report of PCT Application No. PCT/US2009/031957 dated Mar. 30, 2009.
Del Poeta et al., "Amount of spontaneous apoptosis detected by Bax/Bcl-2 ratio predicts outcome in acute myeloid leukemia (AML)," *Blood*, 101(6):2125-2131 (2003).
Matsumoto et al., "Bax to Bcl-2 Ratio and Ki-67 Index Are Useful Predictors of Neoadjuvant Chemoradiation Therapy in Bladder Cancer," *Jpn. J. Clin. Oncol.*, 34(3):124-130 (2004).
Vaskivuo et al., "Apoptosis and Apoptosis-Related Factors Bcl-2, Bax, Tumor Necrosis Factor-α, and NF-κB in Human Endometrial Hyperplasia and Carcinoma," *Cancer*, 94(7):1463-1471 (2002).
Wachsberger et al., "Tumor Response to Ionizing Radiation Combined with Antiangiogenesis or vascular Targeting Agents: Exploring Mechanisms of Interaction," *Clin. Cancer Res.*, 9:1957-1971 (2003).
David S. Goodsell, "The Molecular Perspective: Cytochrome c and Apoptosis", The Oncologist 9:226-227 (2004).
Alessandro et al., Proteomic strategies and their application in cancer research. Tumori. Nov.-Dec. 2005;91(6):447-55.
Anderson et al., Methods and biomarkers for the diagnosis and prognosis of cancer and other diseases: towards personalized medicine. Drug Resist Updat. Aug.-Oct. 2006;9(4-5):198-210.
Boddy, et al., The androgen receptor is significantly associated with vascular endothelial growth factor and hypoxia sensing via hypoxia-inducible factors HIF-1a, HIF-2a, and the prolyl hydroxylases in human prostate cancer. Clin Cancer Res. Nov. 1, 2005;11(21):7658-63.

(Continued)

*Primary Examiner* — Lei Yao
(74) *Attorney, Agent, or Firm* — McCarter & English, LLP; Jill Mello (57) ABSTRACT

Systems and kits are provided which are capable of determining the oncogenicity of a cancer, tumor progression, and effectiveness of a cancer treatment. Such systems and kits utilize assays to examine the levels of apoptotic markers, angiogenesis markers, immunomodulation markers, and cell cycle markers and can compare samples from a patient taken at different times to determine the oncogenicity of a cancer, tumor progression, and effectiveness of a cancer treatment. Methods for determining the oncogenicity of a cancer, tumor progression, and effectiveness of a cancer treatment with such systems and kits are also provided.

16 Claims, 4 Drawing Sheets

(56) References Cited

OTHER PUBLICATIONS

Koyanagi, The circadian rhythm of angiogenesis and chronotherapeutics. Kekkan Igaku (Vascular Biology & Medicine). Nov. 15, 2007;8(4):363-369.

Lavrik et al., Death receptor signaling. J Cell Sci. Jan. 15, 2005;118(Pt 2):265-7.

Mazzanti et al., Differential expression proteomics of human colon cancer. Am J Physiol Gastrointest Liver Physiol. Jun. 2006;290(6):G1329-38.

Ouellet et al., An apoptotic molecular network identified by microarray: on the TRAIL to new insights in epithelial ovarian cancer. Cancer. Jul. 15, 2007;110(2):297-308.

Tanaka et al., Antiangiogenic Agents. Kan-Tan-Sui (Liver-Bile Duct-Pancreas). Nov. 28, 2006;53(5):903-915.

\* cited by examiner

*Apoptotic Protein Expression*

Apoptosis Rating:

*Scale:* 1 *(low apoptotic resistance)* – 15 *(very resistant to apoptosis)*

*Sample:* 13

*Summary:* The sample shows a high resistance to apoptosis.

FIGURE 1

*Angiogenesis Protein Expression*

Angiogenesis Rating:
    *Scale:* 1 *(low rate of angiogenesis)* – 15 *(high rate of angiogenesis)*

*Sample:* 11

*Summary:* Compared to normal tissue there is a significant increase in angiogenesis.

FIGURE 2

*Immunomodulatory Protein Expression*

Immunomodulatory Rating:

*Scale:* 1 *(low involvement of immunomodulation in tumor progression)* – 15 *(Immunomodulatory factors play a high role in tumor progression)*

*Sample:* 9

*Summary:* There is a slight influence of immunomodulatory factors in tumor progression.

FIGURE 3

*Cell Cycle Protein Expression*

Cell Cycle Rating:

*Scale:* 1 *(High inhibition by p21/p27)* – 15 *(Low inhibition by p21/p27)*

*Sample:* 11

*Summary:* There is a low inhibition of the cell cycle activity - active multiplication of cancer.

FIGURE 4

ASSAY SYSTEM FOR THE ASSESSMENT OF ONCOGENICITY, TUMOR PROGRESSION, AND TREATMENT EFFICACY

CROSS-REFERENCE TO RELATED APPLICATIONS

This application claims the benefit of and priority to U.S. Provisional Application Ser. No. 61/023,570, filed Jan. 25, 2008, the entire disclosure of which is incorporated by reference herein.

BACKGROUND

Cancer is presently one of the leading causes of death in developed nations. Recent research has vastly increased the understanding of many of the molecular mechanisms of tumorigenesis and has provided numerous new avenues for the treatment of cancer. Systems and methods for assessing the stage of a cancer, as well as its oncogenicity and the extent of tumor progression, are clinically used in an attempt to determine appropriate treatments. Such systems and methods may also be utilized to assess the efficacy of any treatment utilized.

Improved methods for the treatment of diseases, including cancer, which permit assessment of oncogenicity, tumor progression, and treatment efficacy, remain desirable.

SUMMARY

The present disclosure provides assay kits and systems suitable for use in treating cancer. Systems and kits of the present disclosure allow one to determine the cancerous nature of a tissue sample, such as by assessing the stage of a cancer, as well as its oncogenicity and the extent of tumor progression. The kits and systems of the present disclosure may also be utilized to determine appropriate treatments as well as the efficacy of any treatment utilized. In embodiments, systems and kits of the present disclosure may utilize assays, in embodiments ELISA, to examine the levels of apoptotic markers, angiogenesis markers, immunomodulation markers, and/or cell cycle markers, and can compare samples from a patient taken at different times to determine the oncogenicity of a cancer, tumor progression, and effectiveness of a cancer treatment.

In embodiments, a kit or system of the present disclosure may utilize a software program to analyze the data generated by the assays of the present disclosure. In embodiments, a kit or system of the present disclosure may include an assay for measuring a level of a protein in a tissue sample implicated in a cellular process such as apoptosis, angiogenesis, immunomodulation, cell cycle development, and combinations thereof; and at least one processor coupled to a computer-readable media configured to store a set of instructions capable of being executed by the at least one processor, the instructions including comparing a level of the protein in the tissue sample with a baseline value, and determining whether or not the tissue sample is cancerous.

Methods utilizing such kits and systems are also provided. In embodiments, methods of the present disclosure may include methods for determining the cancerous nature of a tissue sample, such as by assessing the oncogenicity of a cancer, determining the progression of a tumor, determining the efficacy of a cancer treatment, combinations thereof, and the like.

DESCRIPTION OF THE DRAWINGS

Various embodiments of the present disclosure will be described herein below with reference to the figures wherein.

DETAILED DESCRIPTION

The present disclosure provides an assay system that examines cellular proteins that play a vital role in apoptosis (programmed cell death), angiogenesis (new blood vessel growth), immunomodulation, and cell cycle factors thereby contributing to the overall level of oncogenicity. A cancer cell exhibits impaired signaling of the gene/protein expression of factors related to the aforementioned processes. This leads to: an imbalance of homeostasis; loss of immune surveillance and apoptotic control; mutations from tumor-induced autoregulation; and increased vasculature. These combine to be the precipitating factors that drive the onset of oncogenesis. For example, an increase of Bcl-2 expression, which prevents apoptosis, combined with a downregulation of Bax expression, may be indicative of apoptotic resistance. Thus, measuring the expression of proteins like Bax and Bcl-2 before and after a cancer treatment may lend insight into whether a treatment regimen effectively restores the apoptotic potential to malignant tissue.

In accordance with the present disclosure, systems and kits are provided including multiple assays which may be utilized to assess the malignancy of a cancer, including its oncogenicity, as well as the progression of tumors and the effectiveness of treatments. An apoptosis assay component of the system may be utilized to indicate whether cells are undergoing programmed cell death at a normal rate, or whether the cells are not dying as they should, which could be indicative of the malignant nature of the cells. An angiogenesis assay portion of the system may measure the secretions and cellular receptors of cancer cells to determine their ability to stimulate the formation of new blood vessels which may provide nutrients to facilitate tumor growth.

These values may be utilized to quantify the progression of a tumor and the efficacy of anti-angiogenic treatments. Immunomodulation measurements may be utilized to indicate the immune response for uncontrolled growth of cells and the level of infiltration into the tumor microenvironment. Finally, cell cycle factors may be utilized to assess the rate of cell turn over, which is indicative of the how aggressively the tumor may be growing.

The four categories (apoptosis, angiogenesis, immunomodulation, and cell cycle factors) may be rated on a numeric scale individually, however a clinician may assess the four given values collectively, to monitor and choose and follow a treatment regimen for a malignancy.

A technological advantage of an assay system or kit of the present disclosure includes the software accompanying the system or kit which will analyze proteins to rate tumor progression and the efficacy of a treatment in a simple numerical reading. In embodiment, levels of as many as 25 proteins may be analyzed to rate tumor progression and the efficacy of a treatment in a simple numerical reading.

Construction of an ELISA Kit:

In embodiments, the assay system of the present disclosure may include an enzyme-linked immunosorbent assay (ELISA) kit. Any ELISA system within the purview of those skilled in the art may be utilized. In embodiments, the ELISA kit may be prepared using a direct pathway. In other embodiments, the ELISA kit may be prepared using an indirect pathway.

For an ELISA kit prepared using a direct pathway, a suitable method for producing the ELISA kit includes the attachment of an antibody of interest to the base of a plastic 96-well plate. A sample is then dispensed into the well and the target protein will bind to the antibodies. After washing off the unreacted proteins, a second monoclonal antibody bound to a recorder enzyme may be added to the wells in the plate. This antibody attaches to the protein complex on the bottom of the wells. Proteins that do not bind to the complex are removed by washing the wells. Subsequently, an enzyme substrate is added to the wells to initiate a reaction with the recorder enzyme. The intensity of the color change depends on the concentration on the bound recorder enzyme correlating to the concentration of the target protein.

For an ELISA kit prepared using an indirect pathway, an indirect method measures the antibodies present in a patient's samples (e.g. serum). An antigen is absorbed in the wall of the 96 well plates. The sample from the patient is added to the well and if the antibody of interest (in the patient's serum) is present, it will bind to the antigen. After washing the unreacted proteins, a second antibody with a recorder enzyme is added to bind with the antibodies present in the patient's sample. Adding an enzyme substrate will produce a colorimetric change and the intensity of the color change will be measured using a UV-Vis spectrometer.

In some embodiments, an assay system of the present disclosure may be based upon a direct ELISA method. The wells of the plate may be coated with antibodies of interest and homogenized samples may be added to the plate to quantify the protein expression of the apoptotic, angiogenic, immunomodulatory, and cell cycle proteins.

Other technologies which may be utilized with an assay system of the present disclosure are within the purview of those skilled in the art and include, but are not limited to, immuno-histochemical, staining, western blot kits, gene expression for the corresponding proteins (including gene constructs for protein expression), and proteonomics studies, which, in embodiments, could include mass-spectroscopy.

The above technologies may similarly be used to quantify the expression of apoptotic, angiogenic, immunomodulatory, and cell cycle proteins, thereby permitting one to determine the cancerous nature of a tissue sample, such as by assessing the stage of a cancer, as well as its oncogenicity and the extent of tumor progression.

Cellular Markers Examined by Assay System

Apoptotic Markers

Any apoptotic markers may be examined using the assay systems of the present disclosure. Such markers include, but are not limited to:

1) Bcl-2: B-cell lymphoma 2 is an anti-apoptotic protein and is upregulated in oncogenic cells.
2) Bax: A pro-apoptotic member of the Bcl-2 protein family, activity is inhibited by increased Bcl-2 levels in >65% of all cancers.
3) Bid: A BH3 subfamily protein that forms dimers with pro/anti and anti Bcl-2 members to trigger the mitochondria to release factors to initiate DNA damage.
4) Cytochrome c: Released in the presence of pro-apoptotic signals and forms complex with Apaf-1 (apoptotic protease activating factor 1: a protein that participates in apoptosis) to initiate activity of CARD family (CARD is the Caspase Recruitment Domain: domains found in proteins that mediate the formation of larger complexes and play a role in processes including, for example, apoptosis). (E.g. Casp-9, Casp-6 and Casp-3.)
5) Caspase-3: Key member of the CARD family that is the end-point cytosolic mediator preceding the initiation of DNA fragmentation in the nucleus.
6) p53: p53 is a transcription factor that regulates the cell cycle and hence functions as a tumor suppressor. It is important in multicellular organisms as it helps to suppress cancer.

Angiogenic Markers

Any angiogenic markers and/or gene constructs may be examined using the assay systems of the present disclosure. Such markers include, but are not limited to:

1) VEGF: Vascular Endothelial Growth Factor. Major protein responsible for development of vascular beds that feed tumor nutrients and provides foundation for metastases. Released by cells to promote new vessel formation
2) HIF-1α: Hypoxia-Inducible Factor 1 alpha. Released by endothelial walls of tumor to decrease oxygen levels (hypoxia) which is conducive to alternate sources of ATP via glycolytic flux. Also upregulates VEGF and hence angiogenesis.
3) bFGF: Basic Fibroblast Growth Factor. Induces endothelial cell replication, migration, and extracellular proteolysis.
4) Angiostatin: Anti-angiogenic factor that inhibits formation of new vessels.

Immunomodulation

Any markers indicative of immunomodulation may be examined using the assay systems of the present disclosure. Such markers include, but are not limited to:

1) TNF-α: Tumor Necrosis Factor-alpha. A pleiotropic cytokine that causes necrosis in some type of tumor cells and promotes growth in other cells.
2) IL-6: Interleukine-6. A pro-inflammatory response secreted by T-cells. IL-6 has been shown to promote tumor growth and is a prognostic indicator of many cancers as it mitigates immune involvement possibly by augmenting angiogenic effect.

Cell Cycle

Any markers indicative of a cell's place in cell cycle development may be examined using the assay systems of the present disclosure. Such markers include, but are not limited to:

1) p21: a cyclin-dependent kinase (cdk) inhibitor, and is a key mediator of p53-dependent cell cycle arrest after DNA damage
2) p27: a cyclin-dependent kinase inhibitor that controls the cell cycle progression at the G1 phase. (The G1 phase is the period in the cell cycle during interphase, before mitosis, cytokinesis, and the S phase. For many cells, this phase is the major period of cell growth during its lifespan.)

Patient Biopsies

In accordance with the present disclosure, in embodiments tissue samples may be taken from a patient and subjected to the assays described above. Any method within the purview of one skilled in the art may be utilized to obtain tissue samples. In embodiments, a biopsy may be utilized to obtain a tissue sample.

For a biopsy, two types of samples may be extracted from a patient. The first sample may be taken from a suspected lesion of abnormal growth. The second sample may be taken from a normal tissue region. These samples may be assayed for the differences in the oncogenic markers described above to determine the cellular difference and the degree of oncogenicity. The samples may be homogenized and placed in a cold lysis buffer containing protease and phosphatase inhibitors to prevent the cleavage and degradation of proteins. In embodiments, the samples may be frozen prior to testing. This may be desirable where there is an extended period of time between obtaining the samples and testing. Any freezing process utilized may assist in the lysing of the cells.

Once the samples are ready for testing, they may be thawed and homogenized. The samples may be centrifuged at about 4° C. to remove any cellular debris not homogenized. Proteins may then be quantified using protein assays that accompany the assay kit.

Kit Design

The assay kit may utilize any suitable assay, including an ELISA assay as described above. In embodiments the kit may utilize an assay prepared by the direct ELISA method described above. Antibodies for the each protein may be affixed to the 96-well plate for the apoptotic, angiogenesis, immunomodulation, and cell cycle proteins.

Apoptosis Assay Section

The kit design includes wells coated with the antibody of interest for a given protein. In some embodiments Bcl-2 may be measured. Standards that accompany the kit may be diluted and added in duplicate to the wells coated with antibodies to Bcl-2. Each of the patient's target samples from a suspected lesion of abnormal growth may then be added to four wells along with the sample of normal tissue such as skin obtained by biopsy from the patient. The Bcl-2 proteins present in the sample will bind to the antibody coated on the base of the plate. The wells may be washed with reagents and a secondary antibody with a recorder enzyme may be added to the wells. The second antibody added will bind to the complex attached to the plate. The wells may be washed and an enzyme substrate may be added and the intensity of the colorimetric assay may be measured using spectroscopy. The other proteins levels are measured using the same concept.

Once the individual protein levels are quantified, the 6 proteins may be compared. Any apoptotic protein may be quantified utilizing these methods. In embodiments, apoptotic proteins that may be quantified utilizing these methods include:

1) Bcl-2
2) Bax
3) p53
4) Bid
5) Caspase-3
6) Cytochrome c

For the above markers, an increase in Bcl-2, or a decrease in Bax, Bid, Caspase-3, Cytochrome C, would be indicative of a decrease in apoptosis, which in turn is indicative of an aggressive cancer. Conversely, a decrease in Bcl-2, or an increase in Bax, Bid, Caspase-3, or Cytochrome c, would be indicative of an increase in apoptosis, which in turn is indicative that a given treatment is effective in treating the cancer.

Software Data Analysis

As noted above, a software program may be included with kits of the present disclosure. As noted above, protein levels may be measured based on the concentration of proteins loaded into each well. Data analysis software that accompanies the kits may measure the level of the protein of interest. for example, in embodiments, the software may measure the level of Bcl-2 compared to Bax levels. These values will be compared to the normal biopsy values to determine a significant difference in Bcl-2 related to Bax levels. A ratio of Bcl-2 expression that is significantly higher than Bax, in embodiments about 3:2, in other embodiments from about 1:1 to about 10:1, would indicate a low level of apoptosis, i.e., this ratio should be accompanied by an overall dysregulation of the Bcl-2 protein family leading to impaired apoptotic control. Any statistical variance low enough to demonstrate clinical significance may be utilized.

In addition, levels of p53, Bid, Caspase-3, and Cytochrome c levels may also be compared to normal tissue samples. If there is a decrease in p53, Caspase-3, Bid, and Cytochrome c, then it may be concluded that the sample contains cells that are resistant to apoptosis, one of the hallmark characteristics of oncogenicity.

Through extensive validation testing, the levels for each cancer cell line may be established, as well as a level to relate the value obtained by the data analysis software to the severity of the cancer. The number scale may be from 1-15, in which case 15 correlates to a high resistance of apoptosis and the diagnosis of an oncogenic cell line.

Initial recordings based upon the above assays may be stored, with a follow-up visit to obtain a second biopsy to quantify any change in the apoptotic potential. This may be utilized to indicate the efficacy of treatment and aid the treating physician in deciding whether to continue treatment or change the treatment regimen before the advancement of the cancer condition.

Angiogenesis Assay Section

Any component indicative of angiogenesis may be analyzed as part of the angiogenesis portion of the assay system of the present disclosure. In embodiments, suitable components that may be examined as part of the angiogenesis portion of the assay system of the present disclosure include:

1) VEGF
2) HIF-1α
3) bFGF
4) Angiostatin

Methods similar to those described above for quantifying the apoptotic factors may be utilized for the comparison of angiogenic factors from target samples obtained from a suspected lesion of abnormal growth with normal tissue. Such a comparison may indicate if cells in a lesion are stimulating the formation of new blood vessels. If there is increased VEGF, HIF-1α, bFGF, and decreased Angiostatin, this may be indicative of angiogenesis and a very aggressive and rapidly organizing tumor environment. Conversely, decreased VEGF, HIF-1α, bFGF, and increased Angiostatin may be indicative of a decrease in angiogenesis and that a given treatment is effective in treating the cancer. The data software described above may rate the increase in angiogenesis on a scale from 1 to 15.

While the above assay is described as one which examines protein expression, it may also be constructed to include an assay for each of the receptors for each of the angiogenic factors.

The results obtained may be utilized to suggest a mode of treatment and, after a follow-up visit and additional sampling from a suspected lesion of abnormal growth, the analysis may be utilized to confirm the efficacy of treatment.

Immunomodulation Assay Section

Any immunomodulator may be assayed as the immunomodulation portion of the assay system of the present disclosure. In embodiments, suitable components that may be examined as part of the immunomodulation portion of the assay system of the present disclosure include:
1) TNF-α
2) IL-6

Samples may be obtained as described above from a suspected lesion of abnormal growth and normal tissue. The levels for samples from a suspected lesion of abnormal growth may be compared to basal levels from the normal tissue samples. These calculations can assess the role of the immune response in the promotion of tumor growth. IL-6 increases with age and stress and may have role in oncogenesis; it has a well established role in the progression of cancer and its relationship to angiogenesis. An increase (up-regulation) of IL-6 may promote tumor progression. TNF-α may promote or inhibit tumor growth depending on the type of malignancy.

The data processed by the software accompanying the kit may be utilized to assess the role of inflammation in the cancer type and, more importantly, in a specific patient. In addition to TNF-α and IL-6, secretions for the receptors of these proteins on the cells may also be quantified. The final value, on a scale of 1-15, where 1 signifies the lowest involvement in immunomodulatory response and 15 is the highest, may be based on protein expression as well as cell receptor activity.

Cell Cycle Assay Section

The turnover rate of cancer cells is extremely high. Thus, with this portion of the assay system, this rate of turnover may be quantified by measuring cell cycle markers. Any cell cycle marker may be assayed utilizing the system of the present disclosure. In embodiments, suitable components that may be examined as part of the cell cycle portion of the assay system of the present disclosure include, but are not limited to:
1) p21
2) p27

Again, samples obtained by biopsy as described above will be subjected to an ELISA assay as described above. Decreased levels of either of the above markers may indicate an increase in cell turnover which, in turn, may signify an aggressively growing tumor. Compared to the normal tissue biopsies, the rating of cell cycle turnover may be rated based on a scale of 1-15, where 1 being a low rate and 15 is the fastest rate of turnover. Values from this assay portion may give an indication of the rate of growth of a tumor. Samples obtained at a follow up visit may be examined for the rate of cell turn over, which can then be utilized to assess if a tumor is advancing at a rapid rate or if a treatment is arresting growth.

System

An example of an assay report (for a hypothetical patient) that may be generated with the software of the system and kit of the present disclosure is set forth on the attached FIGS. 1-4 and below in Tables 1-5. The assay report may include such information as the patient's name, date of birth, an identifying number, the date of the report, a brief summary of the patient history, the suspected diagnosis, combinations thereof, and the like, as well as any other factor deemed relevant to the health care provider.

Figure 1:
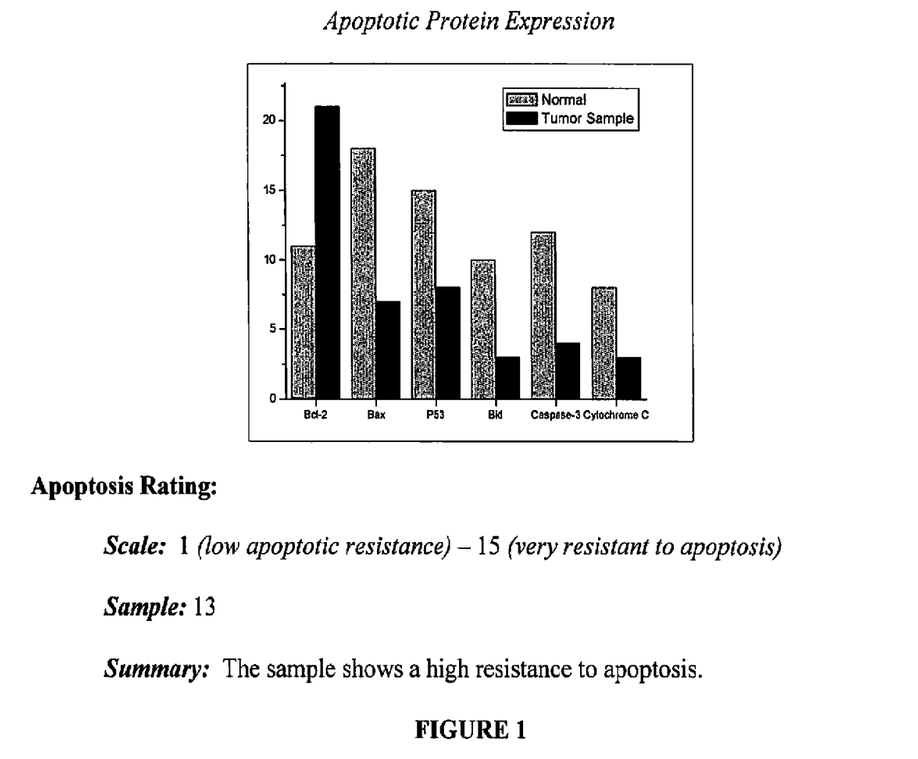
FIG. 1 includes the apoptosis analysis of a sample from an assay report that may be generated with the systems and kits of the present disclosure.
Figure 2:
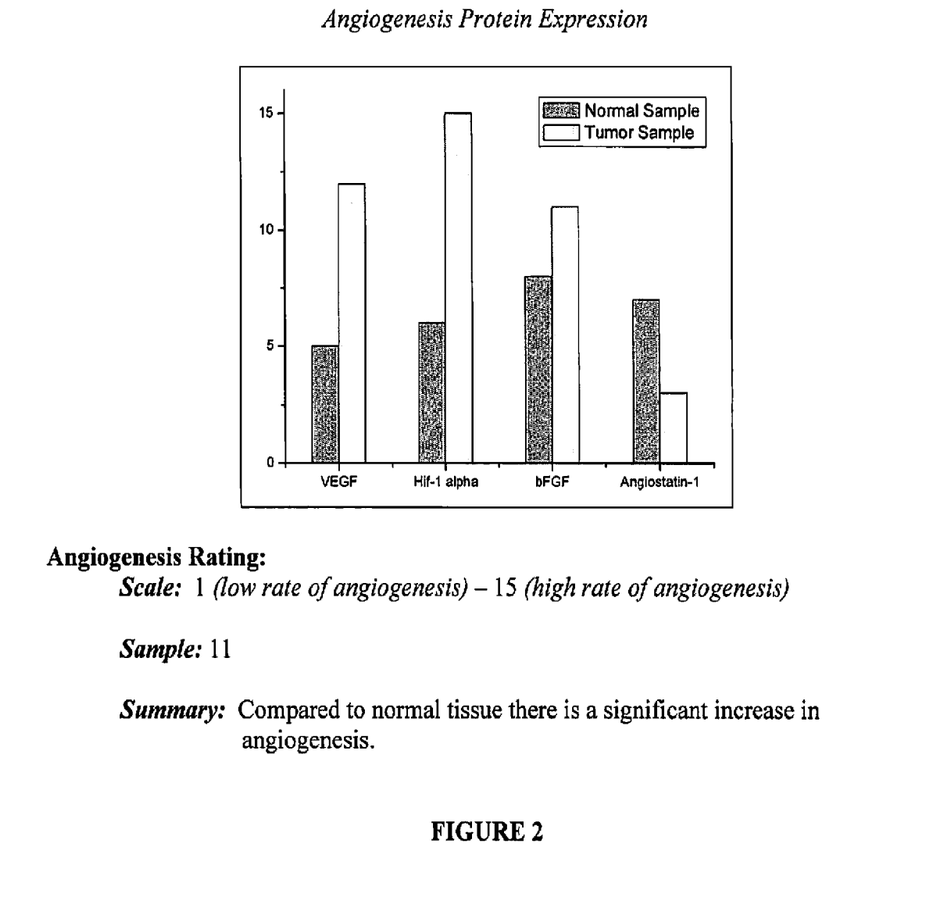
FIG. 2 includes the angiogenesis analysis of a sample from an assay report that may be generated with the systems and kits of the present disclosure.
Figure 3:
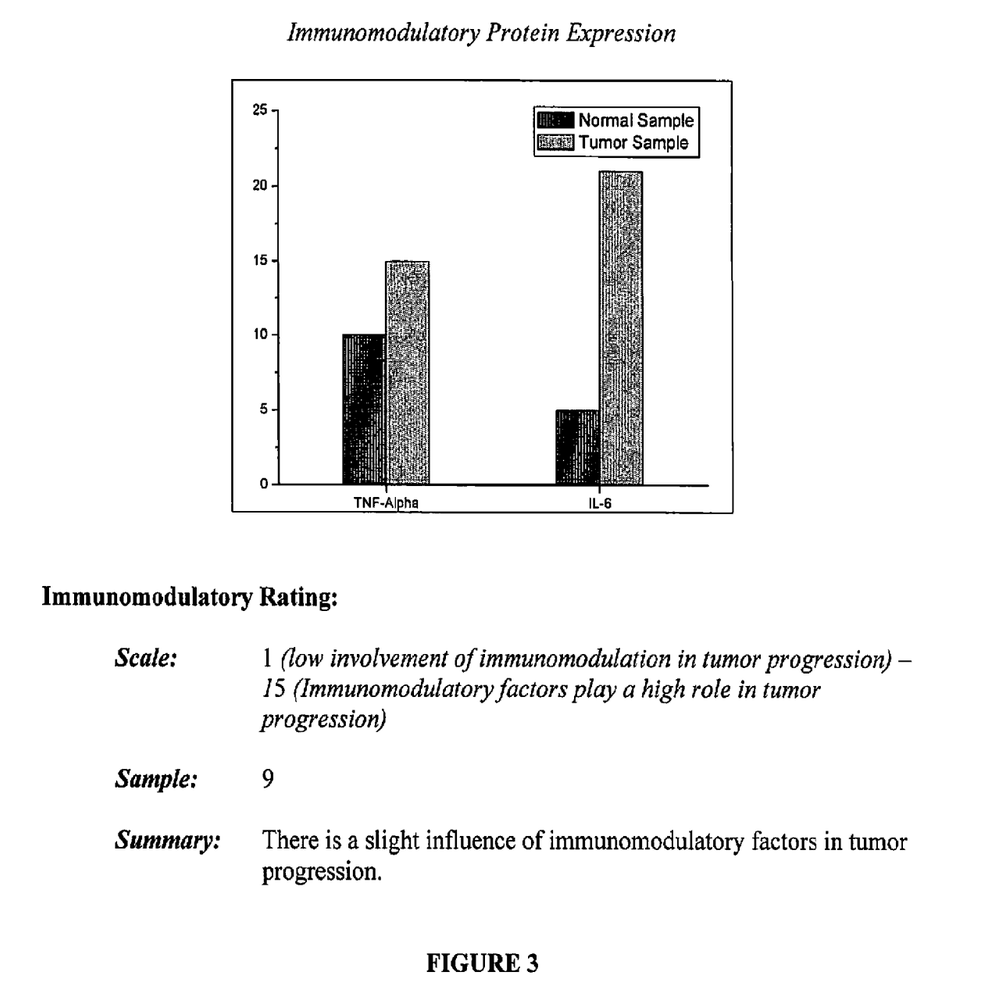
FIG. 3 includes the immunomodulation analysis of a sample from an assay report that may be generated with the systems and kits of the present disclosure.
Figure 4:
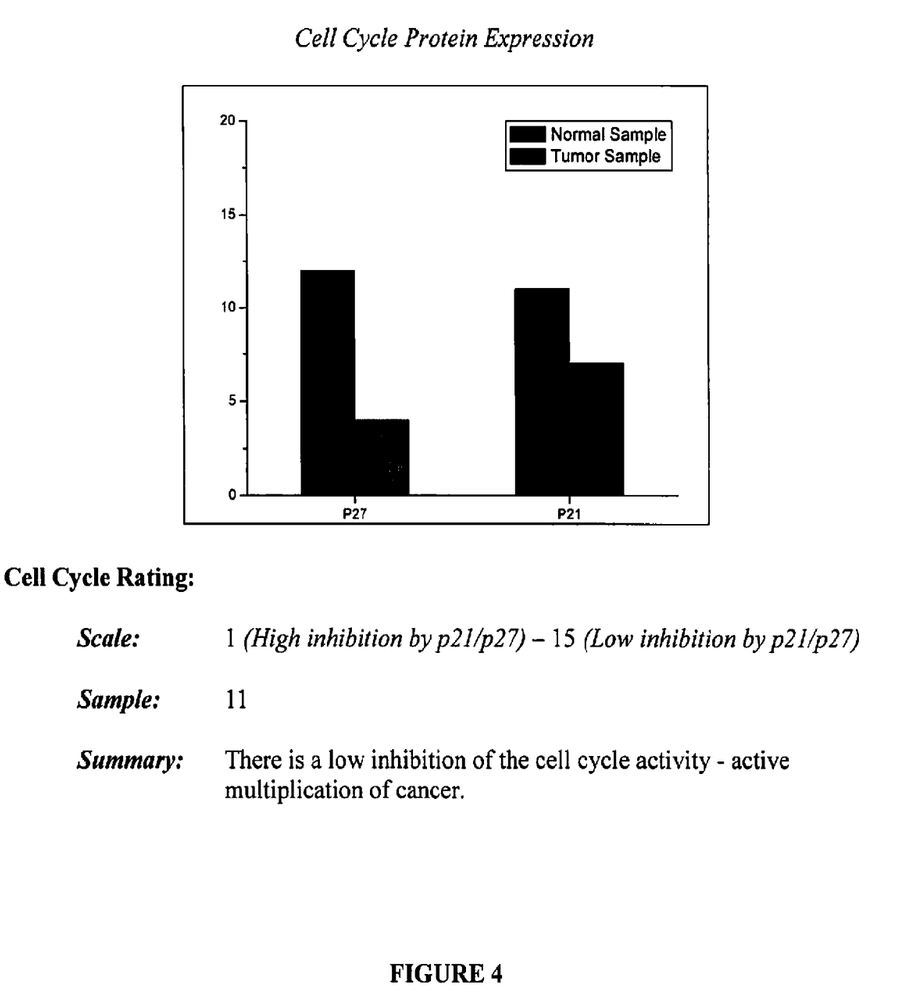
FIG. 4 includes the cell cycle analysis of a sample from an assay report that may be generated with the systems and kits of the present disclosure.

FIG. 1 includes a graph depicting the apoptosis analysis of a sample; FIG. 2 includes a graph depicting the angiogenesis analysis of a sample; FIG. 3 includes a graph depicting the immunomodulation analysis of a sample; and FIG. 4 includes a graph depicting the cell cycle analysis of a sample. In addition to the graphs depicted in the Figures, the assay report (again, in this case for a hypothetical patient) may include the following information included in Tables 1-4 below for each assay (Table 1 for apoptosis, Table 2 for angiogenesis, Table 3 for immunomodulation, and Table 4 for cell cycle analysis), with a sample summary of the assay results as set forth in Table 5 below:

TABLE 1

Apoptosis Results:

| Apoptotic Proteins | Levels Compare to Normal Tissue |
| --- | --- |
| Bcl-2 | Increased |
| Bax | Decreased |
| p53 | Decreased |
| Bid | Decreased |
| Caspase-3 | Decreased |
| Cytochrome C | Decreased |

TABLE 2

Angiogenesis Results:

| Angiogenesis Proteins | Levels Compare to Normal Tissue |
| --- | --- |
| VEGF | Increased |
| Hif-1α | Increased |
| bFGF | Increased |
| Angiostatin-1 | Decreased |

TABLE 3

Immunomodulation Results:

| Immunomodulatory Proteins | Levels Compare to Normal Tissue |
| --- | --- |
| TNF-α | Increased |
| IL-6 | Increased |

TABLE 4

Cell cycle Results:

| Cell Cycle Proteins | Levels Compare to Normal Tissue |
| --- | --- |
| p21 | Decreased |
| p27 | Decreased |

TABLE 5

Summary of Assay results:

| Assay Section | Rating |
| --- | --- |
| Apoptosis | 13 |
| Angiogenesis | 11 |

TABLE 5-continued

Summary of Assay results:

| Assay Section | Rating |
|---|---|
| Immunomodulation | 9 |
| Cell Cycle | 11 |

Clinical Impression:
The data from the main contributing factors to the progression and state of cancer all indicate that the patient has an aggressive malignancy that:
1) Exhibits significant apoptotic resistance that may present problems toward chemotherapeutic intervention.
2) Increased angiogenesis that is facilitating active nutrient delivery to tumor microenvironment and forming vascular armors within and around malignancy to strengthen extracellular complexes which dock tumor site and possible allow metastatic invasion into other tissue/organ sites.
3) The tumor is growing at an extremely high rate. The rate of cell turnover and multiplication is consistent with a tumor that will enlarge quickly and/or invade surrounding tissue, possible leading to metastases based on heterogeneity.
4) The inflammatory factors are increased which suggest that tumor is in proliferative and healthy state. The tumor is developing, "its own immune system" which adds another layer of resistance towards an array of treatment modailites and mediates communication within tumor microenvironment.

It is to be understood that the software component of the present disclosure may be implemented in various forms of hardware, software, firmware, networks, special purpose processors, or a combination thereof. In embodiments, the present disclosure may be implemented in software as an application program tangibly embodied on a program storage device. The application program may be uploaded to, and executed by, a computer system comprising any suitable architecture such as a personal computer, a workstation or server. In embodiments, the system may be implemented on a computer platform having hardware such as one or more central processing units (CPU) (e.g., processor), a random access memory (RAM), a read only memory (ROM) and input/output (I/O) interface(s) such as a keyboard, cursor control device (e.g., a mouse or joystick) and display device. Any similar data processing apparatus capable of operating the software described herein, thereby generating the data described herein may be utilized.

In embodiments, for example, a suitable system may include at least one processor coupled to a computer-readable media configured to store a set of instructions capable of being executed by the at least one processor, the instructions including comparing a level of a protein in a tissue sample with a baseline value, and determining whether or not the tissue sample is cancerous. In such a case, the set of instructions being executed by the at least one processor may include the software component noted above.

In other embodiments, the systems and kits may not include a computer, with the expectation that the user of a system or kit of the present disclosure will possess a CPU or similar processor/apparatus on which the software component of the system or kit may run, thereby generating the data described herein.

In yet other embodiments, a system and kit of the present disclosure may include a stand-alone unit possessing a processor with the software described herein and a reader capable of reading plates or other media/components utilized in the assay of the present disclosure. Examples of such systems include, but are not limited to, those commercially available as the NANOCF™ biological assay system from Eksigent Technologies (Dublin, Calif.).

It will be appreciated that various of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. A method for diagnosing and treating cancer in a subject, comprising:
   (i) detecting in a tissue sample obtained from a suspected lesion of abnormal growth from the subject a decrease in total cellular protein level of Cytochrome C and proteins implicated in apoptosis comprising Bax, p53, Bid, and Caspase-3, based on comparison with a baseline value of the proteins;
   (ii) detecting in the tissue sample an increase in total cellular protein level of two or more proteins implicated in angiogenesis, wherein the proteins are selected from the group consisting of VEGF, HIF-1α, and bFGF, based on comparison with a baseline value of the proteins;
   (iii) determining that the tissue sample is cancerous, exhibits angiogenesis indicative of an aggressive cancer, and exhibits significant apoptotic resistance to chemotherapy treatment; and
   (iv) administering a non-chemotherapy or anti-angiogenic cancer treatment to the subject based on the determination in step (iii).

2. The method of claim 1, further comprising detecting an increase in total cellular protein level of Bcl-2, based on a comparison with a baseline value of the protein, wherein an increase in Bcl-2, a decrease in Cytochrome C, and a decrease in Bax, p53, Bid, and Caspase-3 is indicative of a decrease in apoptosis.

3. The method of claim 2, wherein the decrease in apoptosis is indicative of an aggressive cancer.

4. The method of claim 1, wherein the method further comprises detecting an increase in total cellular protein level of IL-6.

5. The method of claim 1, wherein the method further comprises detecting a decrease in total cellular protein level of a protein implicated in cell cycle, wherein the protein is selected from the group consisting of p21 and p27.

6. The method of claim 1, wherein the baseline comprises a known level of the proteins.

7. The method of claim 1, wherein the baseline is obtained from a sample obtained from a normal tissue region in the animal.

8. The method of claim 1, wherein an increase in the total cellular protein level of three or more proteins implicated in angiogenesis is detected.

9. The method of claim 1, wherein an increase in the total cellular protein level of VEGF, HIF-1α, and bFGF is detected.

10. The method of claim 1, further comprising detecting a decrease in total cellular protein level of angiostatin, wherein the increase in total cellular protein level of VEGF, HIF-1α, or bFGF, and the decrease in total cellular protein level of angiostatin is indicative of an increase in angiogenesis.

11. The method of claim 10, wherein the increase in angiogenesis is indicative of an aggressive cancer.

12. A method for diagnosing and treating cancer in a subject, comprising:
   (i) detecting in a tissue sample obtained from a suspected lesion of abnormal growth from the subject a decrease in total cellular protein level of Cytochrome C, p53, Caspase 3 and Bid, based on a comparison with a baseline value of the proteins;
   (ii) determining that the tissue sample is cancerous and exhibits significant apoptotic resistance to chemotherapy treatment; and (iii) administering a non-chemotherapy cancer treatment to the subject based on the determination in step (ii).

13. The method of claim 12, wherein the method further comprises detecting an increase in total cellular protein level of IL-6.

14. The method of claim 12, wherein the method further comprises detecting a decrease in total cellular protein level of a protein implicated in cell cycle, wherein the protein is selected from the group consisting of p21 and p27.

15. The method of claim 12, wherein the baseline comprises a known level of the proteins.

16. The method of claim 12, wherein the baseline is obtained from a sample obtained from a normal tissue region in the animal.

* * * * *